United States Patent [19]
Crison et al.

[11] Patent Number: 5,993,858
[45] Date of Patent: Nov. 30, 1999

[54] METHOD AND FORMULATION FOR INCREASING THE BIOAVAILABILITY OF POORLY WATER-SOLUBLE DRUGS

[75] Inventors: John R. Crison; Gordon L. Amidon, both of Ann Arbor, Mich.

[73] Assignee: Port Systems L.L.C., Ann Arbor, Mich.

[21] Appl. No.: 08/867,161

[22] Filed: Jun. 13, 1997

Related U.S. Application Data

[60] Provisional application No. 60/019,797, Jun. 14, 1996.

[51] Int. Cl.$^6$ ........................................................ A61K 9/10
[52] U.S. Cl. .......................... 424/490; 424/455; 424/498; 514/937
[58] Field of Search ..................................... 424/489, 490, 424/455, 497, 498; 514/937, 938

[56] References Cited

U.S. PATENT DOCUMENTS 4,540,602  9/1985  Motoyama et al. ................. 427/213.31

OTHER PUBLICATIONS

Farah, N., Laforet, J.P., Denis, J., Self Micro Emulsifying Drug Delivery Systems (SMEDDS) For Improving Dissolution of Drugs: In Vitro, In Vivo Evaluations, 1994 AAPS Annual Meeting—San Diego 1994, Gattefossé Patented Technology.

Bird et al., (1960) in *Transport Phenomena*, John Wiley & Sons, New York, Chapters 16 and 21.

Farah et al. (1993) Self–microemulsifying drug delivery systems for improving in–vitro dissolution of drugs. *AAPS Annual Meeting*, Orlando, Florida.

Grundy et al., (1994) Sensitive high–performance liquid chromatographic assay for nifedipine in human plasma . . . *J. Chrom. B. Biomedical Applications*, 654:146.

Hernell et al., (1990) Physical–chemical behavior of dietary and biliary lipids during intestinal digestion . . . *Biochemistry*, 29:2041–2056.

*Remington's Pharmaceutical Sciences* (1975) Hoover, J.E. editor, 15th ed., Mack Publishing Co., Easton, PA, pp. 334–339.

Ritschel (1980) Gastrointestinal absorption of peptides using microemulsions as delivery systems. *Gattefosse*, No. 83, pp. 7–21.

Sarciaux et al., (1995) Using microemulsion formulations for oral drug delivery of therapeutic peptides. *Int'l. Journal of Pharmaceutics*, 120:127–136.

Staggers et al., (1990) Physical–chemical behavior of dietary and biliary lipids during intestinal digestion and absorption . . . *Biochemistry*, 29:2028–2040.

*Primary Examiner*—Thurman K. Page
*Assistant Examiner*—James M. Spear
*Attorney, Agent, or Firm*—Kohn & Associates

[57] ABSTRACT

A self-microemulsifying excipient formulation for increasing the bioavailability of a drug which includes an emulsion including an oil or other lipid material, a surfactant, and a hydrophilic co-surfactant. A method for making a drug delivery system for increasing the bioavailability of a drug by emulsifying at least one drug with a self-microemulsifying excipient comprising an oil or other lipid material, a surfactant, and a hydrophilic co-surfactant and drugs formulated thereby.

12 Claims, 4 Drawing Sheets

METHOD AND FORMULATION FOR INCREASING THE BIOAVAILABILITY OF POORLY WATER-SOLUBLE DRUGS

This application is based on U.S. Provisional Application Serial No. 60/019,797, filed Jun. 14, 1996.

BACKGROUND OF THE INVENTION

1. Technical Field

The present invention generally relates to a pharmaceutical excipient. More particularly, the present invention relates to a pharmaceutical microemulsion excipient and method of making pharmaceutical compositions.

2. Background Art

It is well known in the art that there are solid drugs which are scarcely soluble in water. Due to their low solubilities, these drugs have a correspondingly low degree of bioavailability.

Several prior art processes have been developed in efforts to increase the solubility and, hence, the bioavailability of poorly soluble pharmaceuticals or drugs. One such prior art process discloses the use of water-soluble high-molecular weight substances having low melting points, such as Carbowax, in combination with an insoluble drug. However, compositions prepared by this process possess poor redispersibility in water due to the low melting point and, therefore, are undesirable as pharmaceutical excipients.

Other methods of increasing the aqueous dissolution rate of poorly water-soluble drugs include the use of organic solvents to solubilize the poorly water-soluble drug or pharmaceutical composition. One such method is disclosed in U.S. Pat. No. 4,540,602 to Motoyama et al., issued Sep. 10, 1985, which discloses a process for the preparation of activated pharmaceutical compositions containing a solid drug that is scarcely soluble in water. The method includes the steps of dissolving or solubilizing a solid drug, that is highly insoluble in water, in a low-boiling point hydrophobic organic solvent such as lecithin. The solubilized drug is then emulsified in the presence of a water-soluble, high-molecular weight substance, such as gelatin, and the drug is removed from the emulsion.

The method disclosed in the Motoyama et al. reference solubilizes the drug and then resolidifies/recrystalizes the drug in a water-soluble matrix such as gelatin or lecithin. The Motoyama et al. method requires the use of organic solvents in order to solubilize the drug. This method has several inherent disadvantages or drawbacks. First, since the drug is solubilized and then recrystalized, the recrystalized product must be reidentified since polymorphic changes can occur when the drug is recrystalized in a different solvent than the solvent originally used. Additionally, since the compounds of interest in the Motoyama patent are water-insoluble, organic solvents must be used in order to solubilize the drugs of interest. The use of organic solvents creates further problems with the health and safety aspects of organic solvents and the environmental unfriendliness and safety of organic solvents. All of these factors associated with the use of organic solvents considerably add to the cost of utilizing organic solvents in a method to increase the solubility of water-insoluble drugs as organic solvent recovery and containment devices are very costly. Other known surface active excipients can be affected by gastric pH or can be destructive to the intestinal mucosa.

In recent years, microemulsions have been extensively studied as a potential modality for oral drug delivery. Microemulsions are particularly useful for improving the oral absorption of water insoluble drugs, such as proteins, by utilizing self-microemulsifying drug delivery systems (SMEDDS) to enhance the solubility of the drug in the upper intestine [Ritschel, 1980]. In particular, microemulsions have gained considerable notoriety as drug delivery systems for peptides drugs.

Microemulsion systems contain a surfactant/co-surfactant blend which when added to a two-phase hydrophilic/lipophilic mixture, form a stable, optically clear, isotropic, colloidal system [Sarciaoux et al., 1995].

The interest in the use of microemulsions as oral drug delivery systems stems from their ability to spontaneously form (emulsify) at a given temperature, their considerable solublizing properties, the ability to be sterilized by filtration, and high physical stability [Sarciaoux et al., 1995]. Another desirable feature of these mixtures is their ability to form a microemulsion when exposed to gastrointestinal fluids. This type of behavior makes SMEDDS good candidates for vehicles for the oral delivery of lipophilic or slightly water-soluble drugs.

Farah et al., [1993] utilized SMEDDS technology in order to evaluate its potential for improving the in-vitro dissolution of the model drug indomethacin. Farah et al., [1993] utilized GELUCIRE with as the lipophilic phase, LABRAFAC (saturated $C_8$–$C_{10}$ polyglycolated glyercides, HLB=10) as the surfactant, LAUROGLYCOL (propylene glycol laurate, HLB=4), and TRANSCUTOL (diethylene glycol monoethyl ether) as the co-surfactants, and indomethacin as the slightly water-soluble drug. Farah et al. [1993] found that the higher the HLB value of the surfactant and co-surfactant mixture, the higher the dissolution rate of the water insoluble drug. Farah et al. [1993] also showed that the in vitro dissolution kinetics of indomethacin from the SMEDDS in gastric medium was substantially improved as compared to indomethacin in the marketed powder form. Farah et al. [1993] further state that the performance of SMEDDS can be used to increase to bioavailability, however; Farah et al. [1993] did not teach any mechanism nor provide any data supporting the assertion that increased dissolution rate absolutely corresponds to an increase in the bioavailability of the drug. Additionally, Farah et al. [1993] do not teach nor suggest that the HLB value of the co-surfactant alone plays an important role in enhancing the bioavailability of water insoluble drugs, lipophilic drugs, or peptides. Farah et al. [1993] merely extrapolate that the bioavailability would be increased from the increased in vitro dissolution of indomethacin.

Therefore, it would be advantageous and desirable to have a method of increasing the dissolution and bioavailability of peptides, lipophilic and poorly water-soluble drugs which avoids the drawbacks of the prior art methods. Furthermore, it would be desirable to have a method which is completely aqueous-based in order to avoid the necessity for recharacterization of the pharmaceuticals or drugs according to the solubilization method disclosed above and also eliminating the cost and both health and environmental safety aspects of using organic solvents. It would also be advantageous and desirable to improve drug delivery via gastro-intestinal administration. It would be a further advantage to have a self-microemulsifying excipient formulation in which the bioavailability of poorly water-soluble drugs can be increased by utilizing a co-surfactant having a high HLB which can be applied to a drug in aqueous solution using standard manufacturing and equipment and which is safe and not destructive to the intestinal mucosa.

By combining the method and self-microemulsifying formulation of the present invention with poorly water-soluble drugs or pharmaceutical compositions, optimal advantage can be taken of the potential potency and efficacy of poorly water-soluble drugs by increasing their bioavailability. The present invention provides an improved method and formulation for providing poorly water-soluble drugs with a means for a greater bioavailability which includes all of the aforementioned mentioned advantages.

SUMMARY OF THE INVENTION AND ADVANTAGES

In accordance with the present invention, there is disclosed a self-microemulsifying excipient formulation for increasing the bioavailability of a drug which includes an emulsion including an oil or other lipid material, a surfactant, and a hydrophilic co-surfactant. Also, in accordance with the present invention is a method for making a drug delivery system for increasing the bioavailability of a drug by emulsifying at least one drug with a self-microemulsifying excipient comprising an oil or other lipid material, a surfactant, and a hydrophilic co-surfactant and the drugs formulated thereby.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
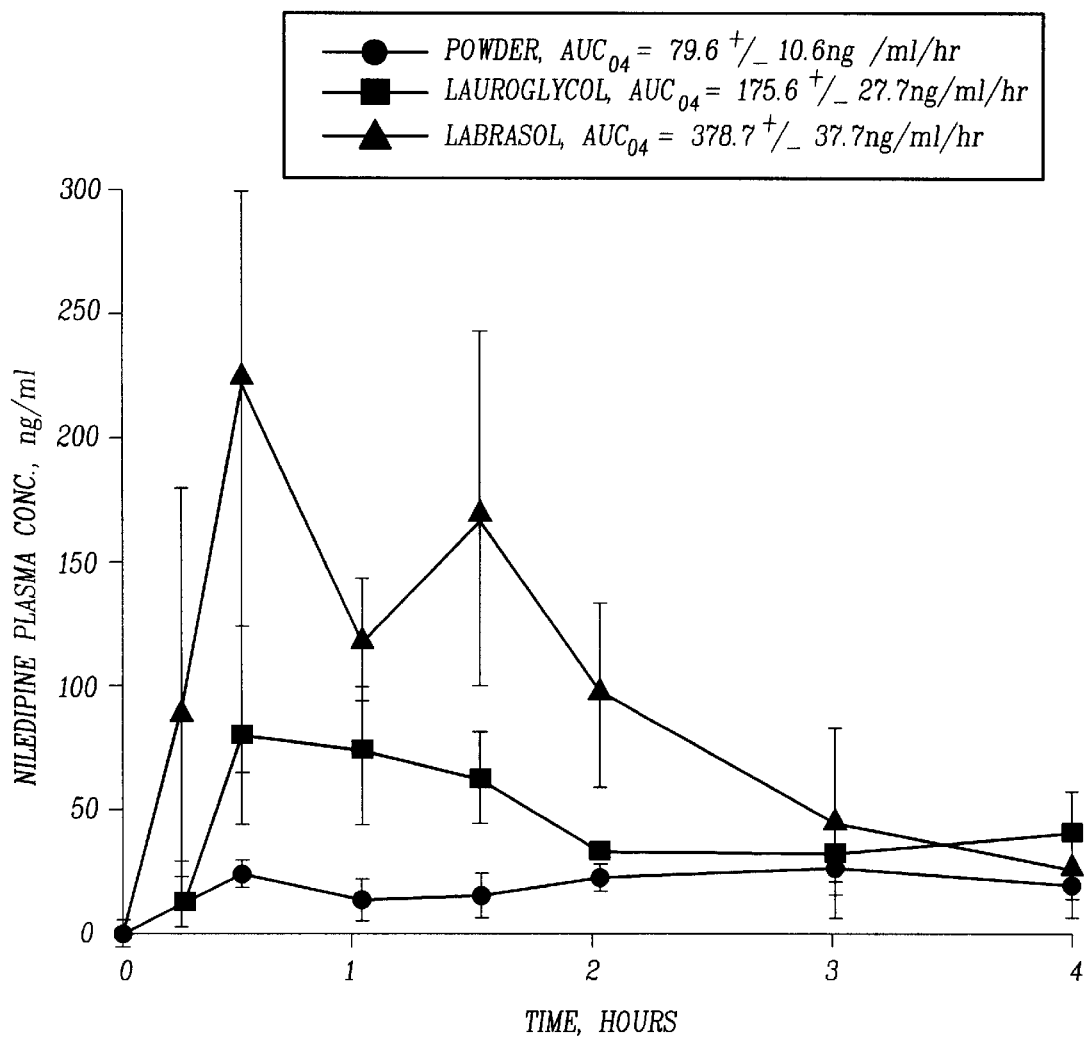
FIG. 1 is a graph illustrating nifedipine plasma concentration versus time profile (average±s.e.m.)

A self-microemulsifying excipient formulation for increasing the bioavailability of poorly water-soluble drugs or pharmaceutical compositions is disclosed. The formulation generally includes an emulsion including an oil or lipid material, a surfactant, and a hydrophilic co-surfactant. A poorly water-soluble drug or pharmaceutical is emulsified in the self-microemulsifying excipient formulation thereby increasing the in vivo bioavailability of the drug or pharmaceutical formulation.

More than one drug or pharmaceutical ingredient and/or formulation at a time can be treated according to the present invention to yield a desired pharmaceutical composition. Additionally poorly water-soluble drugs and/or pharmaceutical ingredients can be treated according to the present invention and can then be used in combination with other drugs and/or pharmaceutical ingredients which may or may not be poorly water-soluble.

The terms "drug" and/or "pharmaceutical ingredient" or "formulation" include any pharmaceutical compound, drug, or composition, including peptides, in a solid form such as powder or granules.

The term "self-microemulsifying" describes a system in which emulsifies when mixed with an aqueous solvent and which, upon exposure to gastrointestinal fluids, forms stable-microemulsions with diameters in the range of 1 $\mu$m.

The oil phase of the self-microemulsifying formulation includes lipid or glycerides containing compounds such as GELUCIRE, Gattefosse Corporation, Westwood, N.J.) but can also include other suitable oil phase compounds for example, digestable or non-digestable oils and fats such as olive oil, corn oil, soybean oil, cottonseed oil, palm oil, and animal fats.

Suitable surfactants or emulsifying agents used in the self-microemulsifying formulation of the present invention include LABRAFAC CM 10, a mixture of saturated $C_8$–$C_{10}$ polyglycolysed glycerides (HLB=10, Gattefosse Corporation, Westwood, N.J.) and other suitable surfactants, for example, long alkyl chain sulfonates/sulfates such as sodium dodecylbenzene sulfonate, sodium lauryl sulfate, and dialkyl sodium sulfosuccinate, quaternary ammonium salts, fatty alcohols such as lauryl, cetyl, and steryl, glycerylesters, fatty acid esters, and polyoxyethylene derivatives thereof. However, the choice of surfactant appears to be less critical than the choice of co-surfactant as discussed below in greater detail.

The co-surfactants suitable for use with the self-emulsifying excipient formulation of the present invention are preferably hydrophilic in nature. In particular, co-surfactants utilized in the present invention should possess an HLB number of greater than 8 based on the HLB system on which is well known to those skilled in the art. The HLB number provides a means for ranking surfactants based on the balance between the hydrophilic and lipophilic portions of the surfactant or emulsifying agent. That is, the higher the HLB number, the more hydrophilic the surfactant or emulsifying agent. In the present invention, the hydrophilic co-surfactant has a hydrophilic-lipophilic balance (HLB) of greater than 8. Typically, surfactants or emulsifiers within HLB in the range of 8–18 form oil/water emulsions. In the present invention, the preferred HLB range for the hydrophilic co-surfactant is between approximately 10 and 14. Additionally, hydrophilic co-surfactants utilized in the present invention are preferably alcohols of intermediate chain length such as hexanol, pentanol, and octanol which are known to reduce the oil/water interface and allow the spontaneous formulation of the emulsion. Preferred hydrophilic co-surfactants utilized in accordance with the present invention include LABRASOL, (Gattefosse Corporation, Westwood, N.J.), which is comprised of medium chain triglycerides derived from coconut oil having an HLB of 14 as well, as other co-surfactants having an HLB of greater than 8 such as lauryl alcohol.

The self-microemulsifying formulation can also include the addition of an aqueous solvent such as triacetin, an acetylated derivative of glycerol, i.e., glyceryl triacetate or other suitable solvents. Triacetin is suitable since it is miscible in the oil/lipid phase and can be used to solubilize a hydrophobic drug.

Additional materials and/or compounds can be added to alter the consistency of the emulsion. This may be done to increase the stability or emolliency of the emulsion. Such materials can include tragacanth, cetyl alcohol, stearic acid, and/or beeswax [Remington's Pharmaceutical Sciences, 1975].

The method of making a drug delivery system for increasing the bioavailability of a drug and/or pharmaceutical ingredient or formulation by emulsifying the drug with the self-microemulsifying excipient formulation of the present invention includes the steps of solubilizing a poorly water-soluble drug, pharmaceutical ingredient, or formulation thereof, in a mixture of surfactant, co-surfactant and solvent. The oil phase can then be suitably prepared, if necessary, by heating or other preparatory means and can then be added to the solubilized drug formulation and thoroughly mixed. The emulsion can then be added to a suitable dosage form such as soft or hard-filled gelatin capsules and allowed to cool.

The relative proportions of surfactant and co-surfactant in the self-microemulsifying formulation of the present invention can influence the solubilizing and dissolution properties of the formulation. In general, the range of concentration of the surfactant/co-surfactant broadly ranges from 15 to 90% (v/v) and more preferably ranges from approximately 45 to 55% (v/v). The concentration of the co-surfactant broadly ranges from 16 to 89% (v/v) and more preferably ranges from 30 to 40% (v/v). The relative amounts of surfactant to co-surfactant in the formulation of the present invention range from approximately 45 to 50% (v/v) with the preferred range being approximately 25 to 35% (v/v). Generally, the ratio of surfactant to co-surfactant ranges from approximately 1:2 to 1:3 depending on the properties of the surfactant and/or the co-surfactant.

The lipophilic, poorly water-soluble active drug or pharmaceutical ingredient utilized in accordance with the present invention can include nifedipine, griseofulvin, cyclosporin, digoxin, itraconozole, carbamazepine, piroxicam, fluconazole, indomethacin, steroids, ibuprofen, diazepam, finasteride, and diflunisal, for example. Other pharmaceutical ingredients or other drugs which are lipophilic or poorly water-soluble can also be used in accordance with the present invention. This list is not meant to be exhaustive, but rather provide examples of suitable compounds may be used in accordance with the present invention.

Applicant has conducted dissolution/bioavailability studies demonstrating the increased dissolution rate of water-insoluble pharmaceutical ingredients and drugs according to the present invention. Specifically, as described in greater detail below, applicant has demonstrated an improvement in the bioavailability of the poorly water-soluble drug, nifedipine, using a co-surfactant with a high HLB (HLB=14) value or that of a co-surfactant with a low HLB (HLB=4) value even though both formulations appeared to solubilize the drug equally. The area under the plasma-time curve (AUC) for the formulation with the high HLB co-surfactant was five times greater than that of the drug alone (powder) and two times greater than that of the formulation with the low HLB value. This result suggested that the HLB value of the co-surfactant plays an important role in increasing the bioavailability of lipophilic or poorly water-soluble drugs by possibly facilitating the solubilization of the poorly water-soluble drugs, by increasing the permeation of the drug across the intestinal wall, or both.

Theoretical considerations of drug dissolution and absorption in the human gastrointestinal tract indicate that for water insoluble drugs two independent variables will control drug absorption: the dissolution rate extent of dissolution and dose of drug given. The significance of this analysis is that for water insoluble drugs, the fraction dose absorbed is inversely proportional to dose and is directly proportion to the dissolution rate. Therefore, in vivo solubilization and dissolution are important determinants of drug absorption.

Intestinal Drug Absorption-Theoretical Considerations

Membrane Permeability and Luminal/Wall Concentration

The fundamental equation describing drug absorption is;

$$J_w = P_w \cdot C_w \quad \text{equation 1}$$

where, $J_w(x,y,z,t)$ is the drug flux (mass/time/area) through the intestinal wall at any position and time, $P_w(x,y,x,t)$ is the permeability of this (complex) membrane, and $C_w(x,y,z,t)$ the drug concentration at the membrane (wall) surface (know as Ficks' First Law) [Bird et al., 1960]. This is Ficks' First Law applied to a membrane and applies at each point along the membrane, i.e., equation 1 is a local law pertaining to each point along the intestinal membrane. Equation (1) states that the critical parameters governing drug absorption are the intestinal permeability and the concentration of drug in solution at the intestinal surface. $P_w$ here is assumed to be high since the drugs are lipophilic. Therefore the focus will be the term $C_w$.

However, the fraction dose absorbed may be independent of the dissolution of the drug if the solubility is very low or the dose very high. This region, termed the solubility limited region of drug absorption, clearly indicates that the extent of drug absorption will be very dependent on the solubility of the drug in the gastro-intestinal luminal contents [Hernell et al., 1990; Staggers et al., 1990; and Davenport, 1982].

Based on the discussion above and the accompanying experimental data, applicant has shown that a more hydrophilic co-surfactant, that is, a co-surfactant with a high HLB number, not only increases the dissolution of poorly water-soluble drugs and pharmaceuticals but, that it also greatly increases the in vivo bioavailability of the poorly water-soluble drug or pharmaceutical. That is, not only is more of the poorly water-soluble drug or pharmaceutical solubilized but, the self-microemulsifying formulation of the present invention also presents the drug or pharmaceutical ingredient to an organism in a form which is more readily utilized and thus, enhances the bioavailability of the drug or pharmaceutical ingredient. Below is an example of this effect.

EXAMPLES

Formulations

The formulations were prepared following the phase diagram of Farah et al. [1993]. Briefly nifedipine was added to a test tube and solubilized in a mixture of surfactant (75 μl LABRAFAC CM 10, Gattefosse Corporation, Westwood, N.J.), co-surfactant (175 μl LAUROGLYCOL, HLB=4 or 175 μl LABRASOL, HLB=14), and aqueous phase solvent (triacetin). GELUCIRE 44/14 (Gattefosse Corporation) was heated to approximately 70° C., and then was added to the nifedipine formulation and the entire mixture vortexed. The resulting formulation in both cases was a clear solution at this temperature. The solution was then added to a size 1, hard gelatin capsules (HGC, Capsugel) and allowed to cool. For the bulk powder formulation, nifedipine was weighed out and added to the hard gelatin capsules at the same dose as the lipid formulations.

Dog Studies

Three male and female mongrel dogs were used to test the formulations. Prior to the study, the dogs were fasted for 18 hours with free access to water. Capsules containing 30 mg of nifedipine (15 mg/capsule) were administered orally as either bulk powder or lipid formulation, with 50 ml of water (n=3). Blood samples (2.5 ml) were taken prior to and at 0.25, 0.5, 0.75, 1.0, 1.5, 2.0, 3.0, 4.0, 5.0, and 6.0 hours after administration. The samples were centrifuged immediately at 4° C. and 1 ml of plasma was transferred to a culture tube and kept frozen at −20° C. until analyzed.

Analytical

Extraction:

Nifedipine standards were prepared in 1 ml dog plasma with final concentrations of 200, 100, 50, 25, 12.5 ng/ml. 50 ml of 1 mg/ml internal standard and 200 ml of 1 M NaOH solution were then added and vortexed for three seconds. Next, 5 ml of MTBE-isooctane (75:25 v/v) was added and vortexed for one minute, then centrifuged at 3000 rpm (1800 g) for five minutes. The upper layer was transferred to a glass tube, evaporated to dryness at room temperature, and reconstituted with 250 ml of mobile phase [Grundy et al., 1994].

HPLC Conditions

Column: Supelco, C-8, 4.6×250 mm, 5 mm
Detection: 350 nm
Flow rate: 1.0 ml/min
Injection: 100 ml
Run time: 20 minutes
Mobile phase: 50:50 methanol/water, pH adjusted to 4.0 with acetic acid and TEA to 1% and 0.03% final concentration, respectively.

Stock Solutions nifedipine: 1 mg/ml in methanol
griseofulvin: 1 mg/ml in methanol

Standard Curve nifedipine: 200, 100, 50, 25, 12.5 ng/ml
griseofulvin: 50 ng/ml

RESULTS AND DISCUSSION

Formulations

At room temperature, the lipid formulations appeared to be physically stable semi-solids. When added to either Simulated Gastric Fluid, without Enzymes, USP or Simulated Intestinal Fluid without Enzymes, USP at 37° C., the formulations formed stable microemulsions up to dilutions of seven to one, aqueous to oil.

Dog Studies

Figure 2:
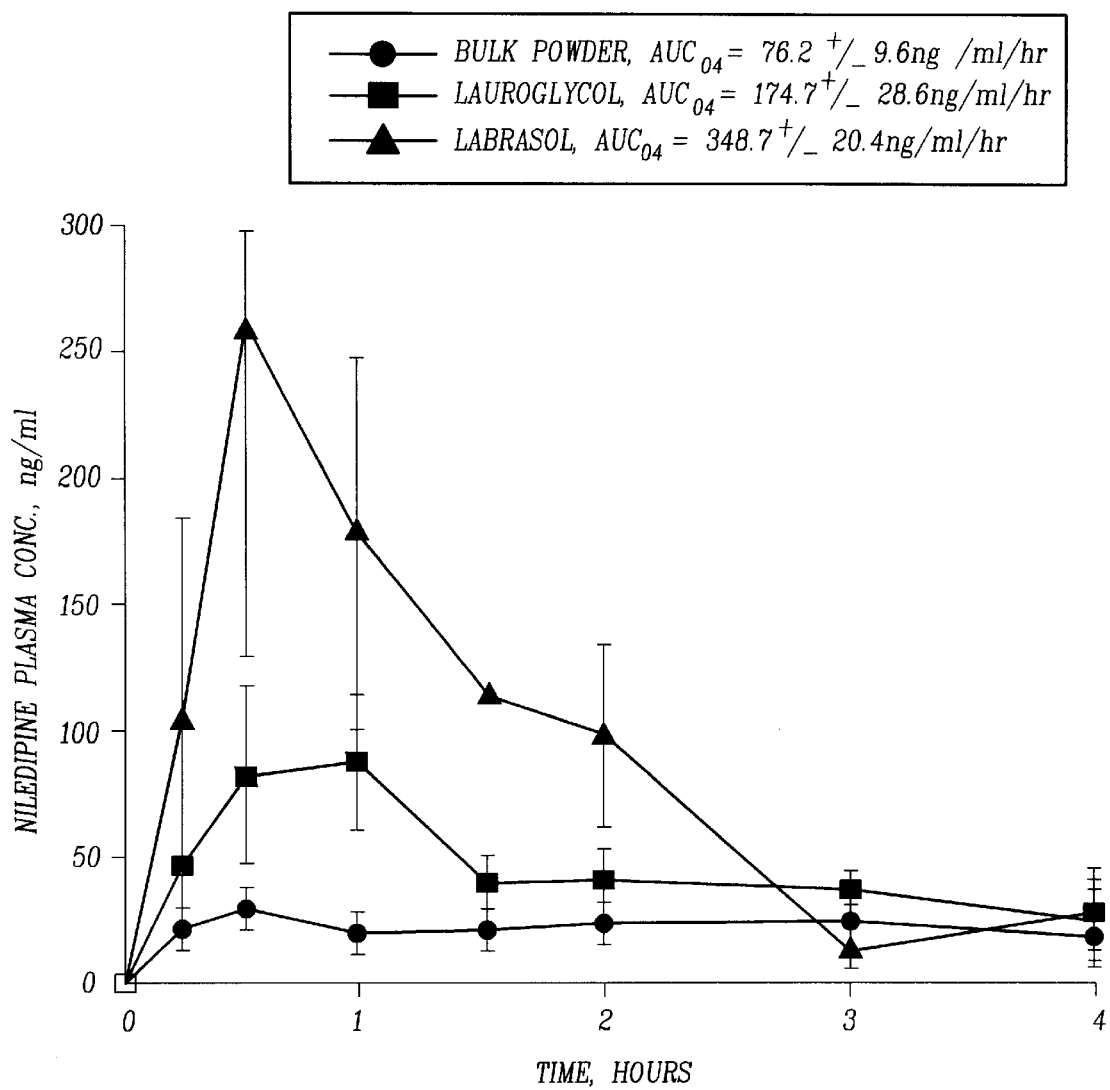
FIG. 2 is a graph illustrating nifedipine plasma concentration versus time profile (average±s.e.m.) adjusted for gastric emptying.
Figure 3:
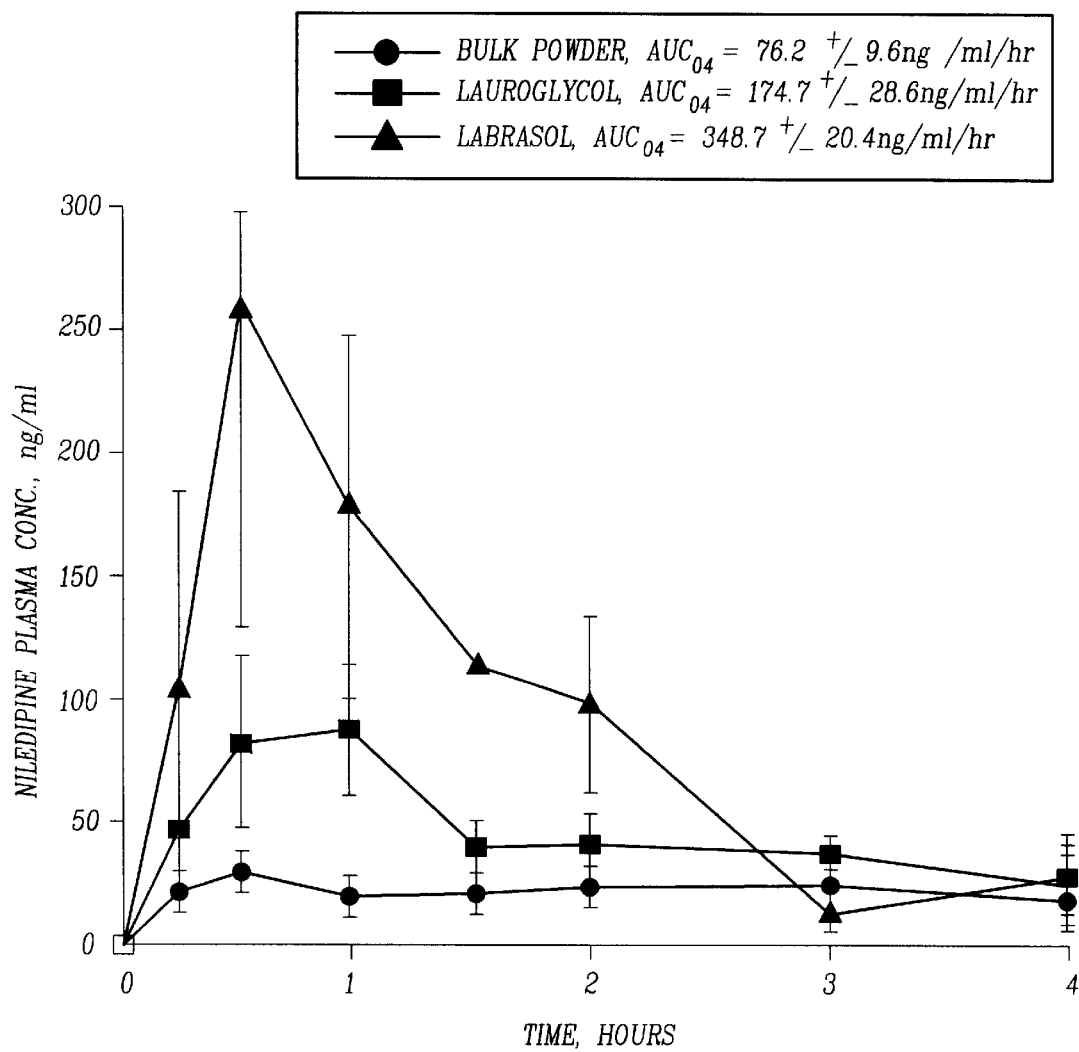
Figure 4:
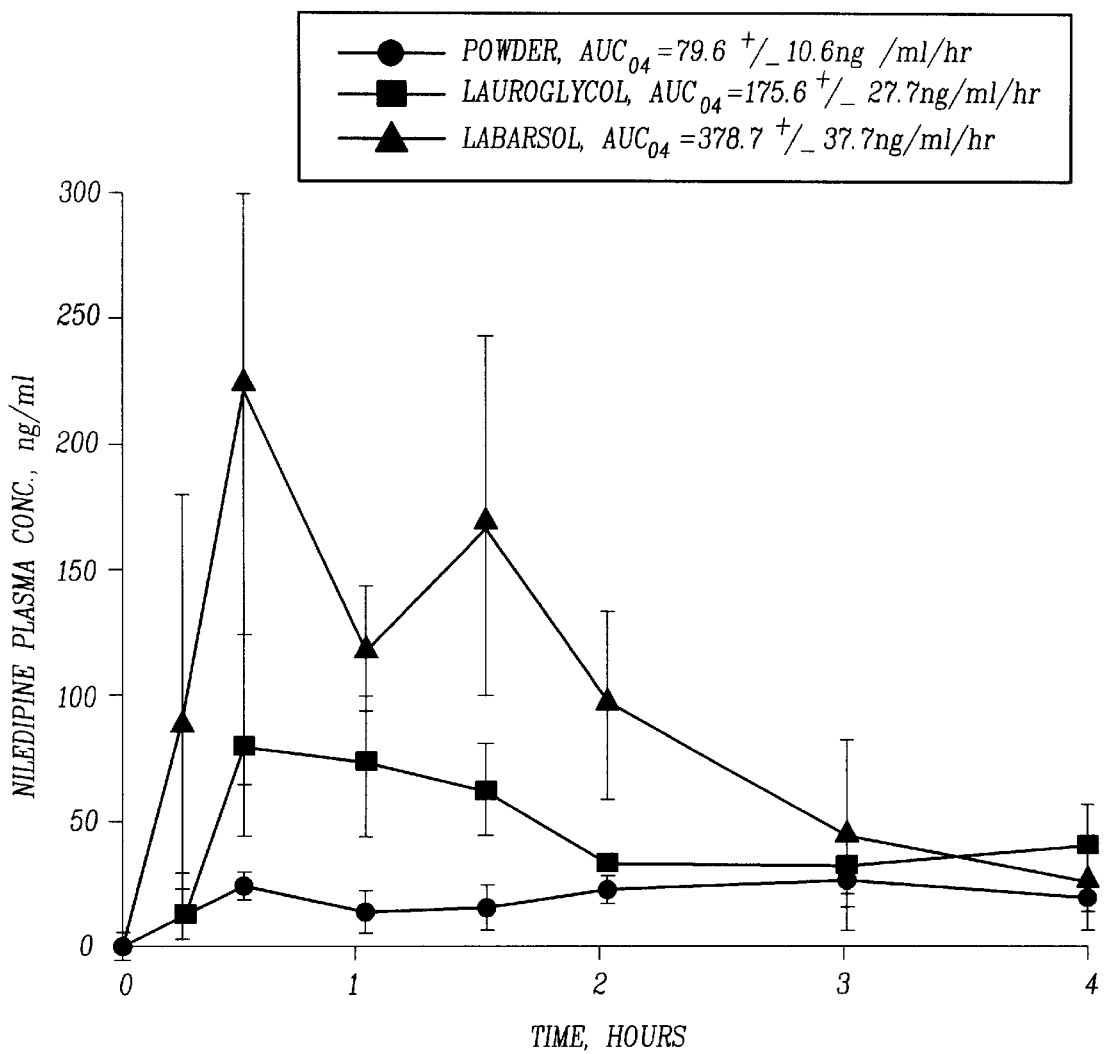

FIG. 1 shows the mean plasma concentration-time profiles for the three treatments in dogs. The $AUC_{0-4}$ (mean±standard error of the mean for these curves are 79.8±10.8, 175.8±27.7 and 378.7±37.7 ng/ml/hr for the bulk powder, formulation containing LAUROGLYCOL (Gattefosse Corporation, Westwood, N.J.) and the formulation containing LABRASOL (Gattefosse Corporation, Westwood, N.J.), respectively. Based on these AUC's, the lipid formulation containing a high HLB co-surfactant was five times greater than that of the powder and two times greater than that of the lipid formulation containing a co-surfactant with the low HLB. Assuming drug absorption immediately follows gastric emptying, the plasma concentrations in FIG. 1 were corrected for gastric emptying by eliminating zero concentrations at early time points as shown in FIG. 2. The $AUC_{0-4}$ for the curves in FIG. 2 are 76.2±9.8, 174.7±28.5 and 348.7±20.4 ng/ml/hr for the bulk powder, formulation containing LAUROGLYCOL and the formulation containing LABRASOL, respectively. While this correction did not change the comparison between the three formulations, it eliminated some of the variability and double peaking.

CONCLUSIONS

The results of these experiments showed that semi-solid lipid filled hard gelatin capsules can be an effective method of improving the oral bioavailabiltiy of water insoluble drugs. A clear trend was shown in the improvement of the bioavailability of nifedipine in dogs using a co-surfactant with a high HLB (HLB=14) value over that of a co-surfactant with a low HLB (HLB=4) value even though both formulations appeared to solubilize the drug equally.

Throughout this application, various publication are referenced by citation and number. Full citations for the publication are listed below. the disclosure of these publications in their entireties are hereby incorporated by reference into this application in order to more fully describe the state of the art to which this invention pertains.

The invention has been described in an illustrative manner, and it is to be understood the terminology used is intended to be in the nature of the description rather than of limitation.

Obviously, many modifications and variations of the present invention are possible in light of the above teachings. Therefore, it is to be understood that within the scope of the appended claims, that the invention may be practiced otherwise than as specifically described.

REFERENCES CITED

Bird et al., (1960) in Transport Phenomena, John Wiley & Sons, New York, Chapters 16 and 21, p. 514.
Davenport, (1982) in Physiology of the Digestive Tract, 5th ed., Year Book Medical Publishers, Inc., Chicago London, p. 212.
Farah et al. (1993) Self-microemulsifying drug delivery systems for improving in-vitro dissolution of drugs. AAPS Annual Meeting, Orlando, Fla.
Grundy et al. (1994) Sensitive HPLC assay for nifedipine in human plasma. J. Chrom. B. Biomedical Applications, 654, 146.
Hernell et al., (1990) Biochemistry, 29:2041–2056.
Remington's Pharmaceutical Sciences, (1975) Hoover, J. E. editor, 15th edition, Mack Publishing Company, Easton, Pa., pp. 334–339.
Ritschel (1980) Gastrointestinal absorption of peptides using microemulsions as delivery systems. Gattefosse, No. 83, pp.7–21.
Sarciaux et al. (1995) Using microemulsion formulations for oral drug delivery of therapeutic peptides. Int'l. Journal of Pharmaceutics, 120:127–136.
Staggers et al., (1990) Biochemistry, 29:2028–2040.

What is claimed is:

1. A self-microemulsifying excipient formulation for increasing the bioavailability of a drug which comprises:
   an emulsion including an oil or other lipid material, a surfactant, and a hydrophilic co-surfactant, said hydrophilic co-surfactant having a hydrophilic-lipophilic balance (HLB) greater than 8.

2. A method for making a drug delivery system for increasing the bioavailability of a drug by emulsifying at least one drug with a self-emulsifying excipient comprising an oil or other lipid material, a surfactant, a hydrophilic co-surfactant, and a solvent which includes triacetin.

3. A self-microemulsifying excipient formulation as set forth in claim 1, wherein said hydrophilic co-surfactant has a hydrophilic-lipophilic balance (HLB) between approximately 10 and 14.

4. A self-microemulsifying excipient formulation as set forth in claim 1, wherein said hydrophilic co-surfactant is an alcohol.

5. A self-microemulsifying excipient formulation as set forth in claim 1 further including a solvent.

6. A self-microemulsifying excipient formulation for increasing the bioavailability of a drug which comprises:

an emulsion including an oil or other lipid material, a surfactant, a hydrophilic co-surfactant, and a solvent including triacetin.

7. A self-microemulsifying excipient formulation as set forth in claim 1, wherein said oil is a lipid.

8. A method for making a drug delivery system for increasing the bioavailability of a drug by emulsifying at least one drug with a self-microemulsifying excipient comprising an oil or other lipid material, a surfactant, and a hydrophilic co-surfactant, wherein the hydrophilic co-surfactant has a hydrophilic-lipophilic balance (HLB) greater than 8.

9. A pharmaceutical ingredient coated with formulation according to claim 1.

10. A method as set forth in claim 8, wherein the hydrophilic co-surfactant has a hydrophilic-lipophilic balance (HLB) between approximately 10 and 14.

11. A method as set forth in claim 8, wherein the hydrophilic co-surfactant is an alcohol.

12. A method as set forth in claim 8 further including the step of solubilizing the drug, surfactant, and co-surfactant in a solvent.

* * * * *